US006478733B1

(12) United States Patent
Weinstein et al.

(10) Patent No.: US 6,478,733 B1
(45) Date of Patent: Nov. 12, 2002

(54) STABILIZING DEVICE HAVING A REMOVABLE PORTION

(75) Inventors: Martin J. Weinstein, South Dartmouth, MA (US); Jennie H. Brown, Providence, RI (US); Douglas A. Hutchison, Suwanee, GA (US); Lawrence F. Travers, Westport, MA (US); Thomas E. Martin, Riverside, RI (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/561,415

(22) Filed: Apr. 28, 2000

Related U.S. Application Data

(63) Continuation-in-part of application No. 09/410,982, filed on Oct. 1, 1999.

(51) Int. Cl.⁷ .................................................. A61B 1/32
(52) U.S. Cl. ........................ 600/213; 600/215; 600/232; 600/231
(58) Field of Search .................................. 600/210, 213, 600/214, 215, 231, 232, 233, 235, 201, 37

(56) References Cited

U.S. PATENT DOCUMENTS

| 2,590,527 A | 3/1952 | Fluck |
| 4,688,570 A | 8/1987 | Kramer et al. |
| 4,702,230 A | 10/1987 | Pelta |
| 5,167,223 A | 12/1992 | Koros et al. |
| 5,231,974 A | 8/1993 | Giglio et al. |
| 5,503,617 A | 4/1996 | Jako |
| 5,509,890 A | 4/1996 | Kazama |
| 5,727,569 A | 3/1998 | Benetti et al. |
| 5,730,757 A | 3/1998 | Benetti et al. |

(List continued on next page.)

FOREIGN PATENT DOCUMENTS

| EP | 0 791 330 A2 | 8/1997 |
| EP | 0 820 721 A1 | 1/1998 |
| EP | 0 993 806 A2 | 4/2000 |
| WO | WO 97/10753 | 3/1997 |
| WO | WO 97/26828 | 7/1997 |
| WO | WO 98/48703 | 11/1998 |
| WO | WO 98/48704 | 11/1998 |
| WO | WO 98/49947 | 11/1998 |
| WO | WO 99/08585 | 2/1999 |
| WO | WO 99/16367 | 4/1999 |
| WO | WO 00/10466 | 3/2000 |

Primary Examiner—Jeffrey A. Smith
(74) Attorney, Agent, or Firm—Richard D. Allison; Thomas J. DesRosier

(57) ABSTRACT

The present invention relates to a stabilizer that immobilizes tissue at a surgical site wherein the device includes a stabilizer having a base portion with elongate extending members that surround the sides of an aperture area and an end portion which is removable from the base portion and which surrounds the remaining side of the aperture area and wherein the stabilizer is preferably used in combination with a pair of flexible connectors that are threaded through the tissue adjacent to the aperture area to draw the tissue into contact with the aperture area of stabilizer and into contact with a pair of tab members extending from the bottom surface of the stabilizer such that the flow of blood through a blood vessel is occluded by tab members when the flexible connectors are releasably attached to the stabilizer.

25 Claims, 6 Drawing Sheets

U.S. PATENT DOCUMENTS

| | | |
|---|---|---|
| 5,749,892 A | 5/1998 | Vierra et al. |
| 5,782,746 A | 7/1998 | Wright |
| 5,799,661 A | 9/1998 | Boyd et al. |
| 5,836,311 A | 11/1998 | Borst et al. |
| 5,865,730 A | 2/1999 | Fox et al. |
| 5,876,332 A | 3/1999 | Looney |
| 5,882,299 A | 3/1999 | Rastegar et al. |
| 5,885,271 A | 3/1999 | Hamilton et al. |
| 5,947,896 A | 9/1999 | Sherts et al. |
| 5,957,835 A * | 9/1999 | Anderson et al. ....... 600/202 X |
| 5,976,080 A | 11/1999 | Farascioni |
| 6,019,722 A | 2/2000 | Spence et al. |
| D421,803 S | 3/2000 | Koros et al. |
| 6,033,362 A * | 3/2000 | Cohn ................. 600/213 |
| 6,036,641 A * | 3/2000 | Taylor et al. .......... 600/235 X |
| 6,050,266 A | 4/2000 | Benetti et al. |
| 6,063,021 A * | 5/2000 | Hossain et al. ............ 600/37 |
| 6,071,295 A | 6/2000 | Takahashi |
| 6,102,854 A * | 8/2000 | Cartier et al. ........... 600/210 X |
| 6,113,534 A * | 9/2000 | Koros et al. ............. 600/213 |
| 6,241,655 B1 * | 6/2001 | Reiss ................... 600/37 |

\* cited by examiner

STABILIZING DEVICE HAVING A REMOVABLE PORTION

The present application is a continuation in part of U.S. Ser. No. 09/410,982 filed on Oct. 1, 1999 (pending).

BACKGROUND OF THE INVENTION

Numerous devices have been used to position tissue at a surgical site to aid in the performing of surgical procedures. Various retractors or similar devices, have been used for many years to hold an artery in position during operations adjacent to the heart to prevent movement of the artery. This serves to minimize the risk of injury to the artery and adjacent tissue and can facilitate the creation of the desired anastomosis.

A recently developed procedure, referred to as the minimally invasive direct coronary artery bypass procedure, has been used to graft onto a coronary artery without cardiopulmonary bypass. This procedure involves the grafting of the left internal mammary artery (LIMA) or saphenous vein onto the left anterior descending (LAD) or other coronary artery. As this procedure does not require the use of a heart lung machine to oxygenate and pump blood, the morbidity and mortality associated with this procedure is substantially lower than previous bypass techniques. A problem associated with the less invasive procedures, however, is that while the heart continues to pump during the procedure, the motion of the heart can interfere with the surgeon's task of attaching the LIMA or saphenous vein to the LAD. There is also a need to stop blood flow in the area of the graft to maintain a clear field of view and provide precise suture placement.

Two basic strategies have been employed to address the problem of operating on a moving site, one being the use of pharmacological agents to limit heart motion, and the other being mechanical, such as a two prong retractor that is pushed down against the heart on both sides of the artery, or alternatively, upward traction away from the moving heart by suction, traction tape or suture thread. Both of these options, however, have problems associated with them. Both options are susceptible to some movement of the vessel graft site. The use of pharmacological agents is undesirable and may impair circulatory function. Traction by compression of the heart requires an increased amount of downward force on the tissue of the heart along a relatively large surface area. Although this type of device does serve to immobilize the tissue at the surgical site, it may also compromise the ability of the heart to maintain circulation and result in hypotension. Upward traction through the use of suction requires that the entire surface of the device be in contact with the tissue of the heart along a relatively large surface area to maintain suction. As with the compression type of devices, the suction type of device may cause injury, stenosis or occlusion of the vessel when upward traction that is sufficient to immobilize the tissue along the surgical site is used. Additionally, because various surfaces of the heart need to be accessed, it is not always possible or convenient to apply compression or upward traction to each surface of the heart.

There is a continuing need for improvement in devices and methods for retaining tissue at surgical sites to further reduce the risks associated with surgical procedures where the devices and methods are inexpensive, versatile, safe and reliable. The increased use of the above-described mechanical devices have also illustrated the need for a device that provides the desired local stabilization while allowing the surgeon to quickly set up and remove the stabilizing device while also providing access to multiple locations and surfaces on the heart of the patient.

SUMMARY OF THE INVENTION

The present invention relates to a cardiac stabilizer for immobilizing tissue at a surgical site and to a method of using the stabilizer during a surgical procedure. A preferred embodiment of the stabilizer includes a generally ovoid or elongate retaining element or platform having an aperture area that exposes the surgical site and a holder that is used to position tissue at the surgical site relative to the retaining element. A handle can be attached to or fabricated with the platform so that the user can manipulate the position of the stabilizer as needed. As used herein, the stabilizer generally refers to a device that is movable into a contacting relationship with the tissue of a patient to reduce the movement of the tissue at the desired surgical site.

The coronary arteries are typically about 1–2 mm in diameter, and the pumping heart can move these arteries over distances of several millimeters during each heartbeat. Because the movement of even 1 or 2 millimeters can result in a displacement of the grafting site that can substantially interfere with suturing an effective anastomosis, it is desirable to restrain movement of the artery at the surgical site in any direction to less than about 1 mm. The stabilizer and tapes of the present invention preferably restrain movement of the tissue relative to the stabilizer.

A preferred embodiment of the invention comprises a retaining element or stabilizer that includes a removable end piece that is removable to form an aperture area that is open to permit removal of the stabilizer from around the grafted artery following the procedure. The end piece is used to contribute to the stability of the stabilizer during the procedure and then is readily removable to allow for the passage of the grafted vessel therethrough. The stabilizer can be beneficial in any procedure where it is desirable to stabilize tissue at a surgical site. For example, the stabilizer can also be used for grafting vessels onto the diagonal, right or other coronary arteries without altering the heart's pumping function or during surgery on various other organs or tissues.

In a preferred embodiment of the invention, a handle or articulating arm may be secured to the platform of the stabilizer and may be held in position by the user, attached to various locations on a retractor frame that is fixed around the operative site or simply clipped to a drape around the site.

In yet another preferred embodiment of the present invention, the stabilizer includes a generally ovoid or elongate shape wherein the lengthwise dimension of the stabilizer is greater than the width dimension. In this form of the invention, the connector for attachment to a handle or other member is located on the stabilizer generally along the an end portion of the stabilizer such that the application of force along the handle is applied over the blood vessel that is to be operated on and near the aperture area.

In a further preferred embodiment, the stabilizer has tape holder elements disposed in the longitudinal dimension and/or along the periphery of the stabilizer. Each holder element includes one or more slots that frictionally grip an end of a connector such as elastic tape or thread which extends through the tissue of the patient to connect the tissue to the stabilizer. The use of slots or grooves on the surface of the stabilizer allows the user to place the connectors such as elastic tape or thread around the outer surface of the stabilizer to position tissue at the surgical site within the stabilizer aperture and to minimize movement of the tissue relative to the stabilizer during the procedure. When these slots are used, the tapes are threaded through the tissue of the heart-wall of the patient and then aligned and drawn towards each other to be positioned in recessed areas along the periphery of the stabilizer. When the tapes are located in the recessed areas, the tapes are then drawn away from each other to be positioned in the desired retaining slots on the holding members. The surgeon can include additional tissue around the blood vessel as the tapes are tightened so that the blood vessel is compressed by the adjacent tissue rather than being directly constricted by the tapes. Additionally, the surgeon can position the tapes at a relatively wide angle of approach when the tapes are threaded around the outer surface of the stabilizer so that more tissue is positioned between the tapes and the blood vessel. The route used by the surgeon varies depending on the depth of the desired blood vessel and the surgeon's preferred approach to performing the anastomosis. The combination of the stabilizer and the tapes provides a system that does not require the significant compression or upward traction as required by the prior devices to obtain a suitable surgical site.

In a further preferred embodiment, the stabilizer may also include a plurality of tabs extending downwardly from the bottom surface of the stabilizer along the ends of the aperture area. The use of the tabs in combination with the tapes causes the tissue in the aperture area to be raised upwardly a small amount to expose the portion of the blood vessel that is to be the subject of the anastomosis. Additionally, the tabs preferably extend downwardly from the ends of the aperture area to create contact surfaces along the ends sides of desired surgical site to further restrict the flow of blood through the blood vessel during the procedure.

When the present invention is used in a coronary artery bypass procedure, the stabilizer is positioned in a desired position along the myocardial surface of the patient. One or more tapes, for example, silastic tape (i.e. a silicon elastomer) or suture thread, are passed through the myocardium at a location adjacent to the artery grafting site with a blunt needle. The stabilizer is then loosely positioned in the desired relative position along the myocardium of the patient. Both ends of each tape are connected to the stabilizer platform with sufficient tension to draw the tissue into contact with the bottom surface of the platform and to occlude blood flow on the upstream side of the operative site. The stabilizer is then securely positioned in the desired relative position along the myocardium of the patient. The tape compresses the artery against the bottom surface of the platform and preferably against the tabs while the artery graft site is held in a fixed position relative to the aperture area. The coronary artery is opened longitudinally and the end of the mammary artery or other blood vessel is sewn to the graft opening with multiple fine sutures. Once the graft is completed, the end portion of the stabilizer may be removed to open the aperture area. The tape may then be released to restore blood flow to the blood vessel and the anastomosis is then inspected for hemostasis and other defects. The anastomosis is then readily removable from the end of the stabilizer through the open end of the aperture area.

Figure 1:
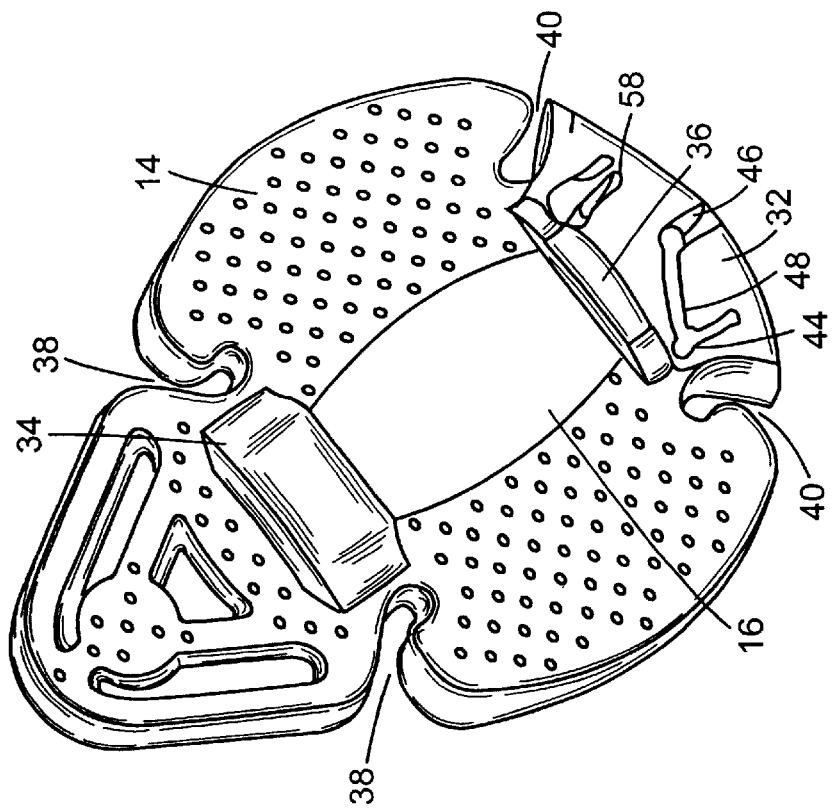
FIG. 1 is a top perspective view of a stabilizer in accordance with the preferred embodiment of the invention.
Figure 2:
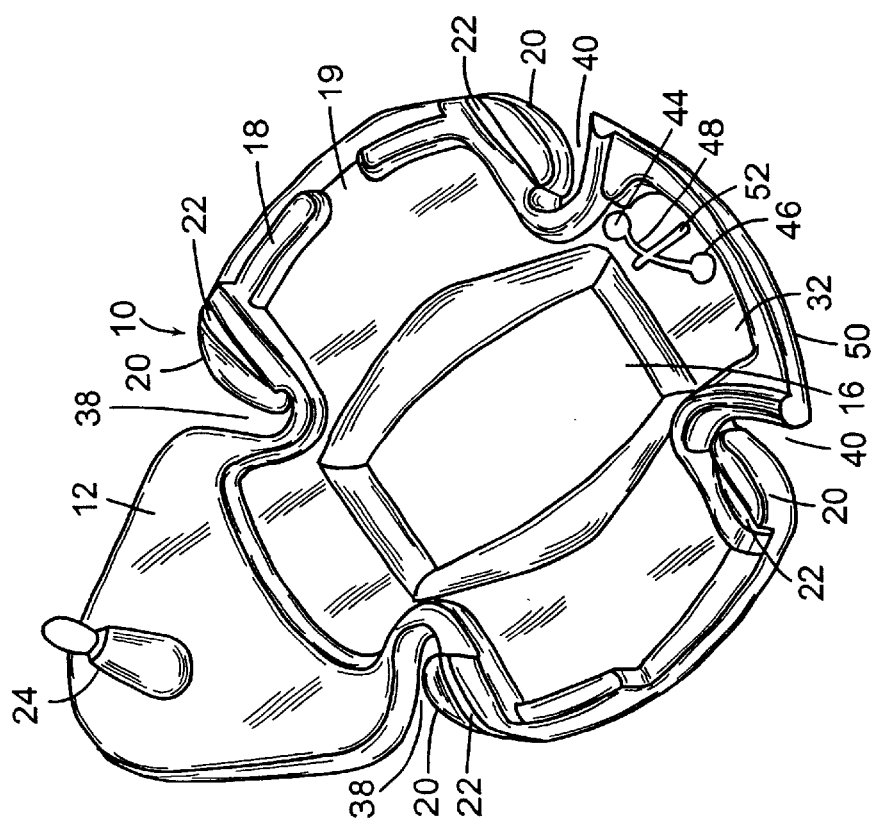
FIG. 2 is a bottom perspective view of the stabilizer in accordance with the preferred embodiment of the invention.
Figure 4:
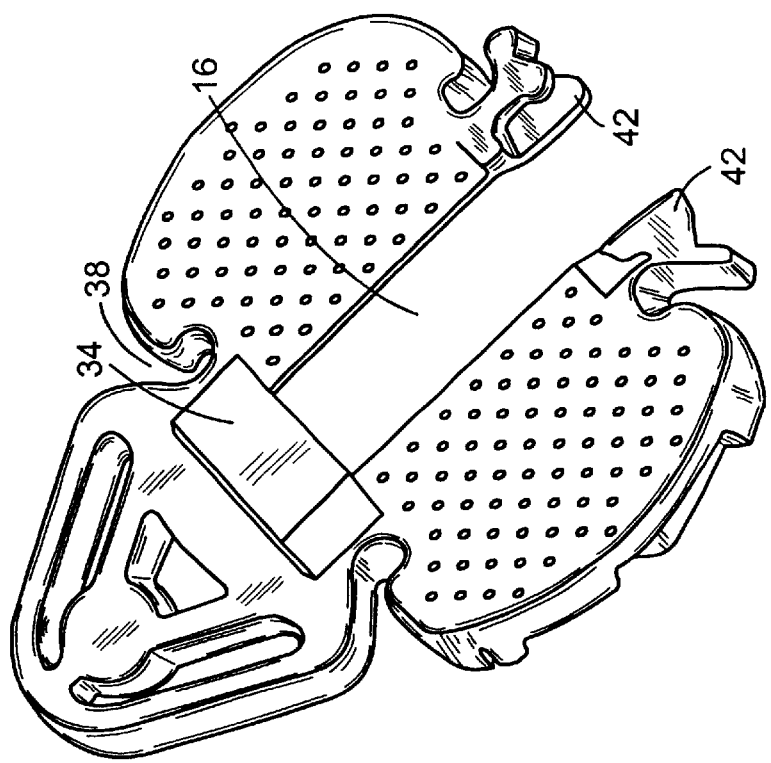
FIG. 4 is a bottom perspective view of the stabilizer in accordance with the preferred embodiment of the invention having the end portion removed.
Figure 3:
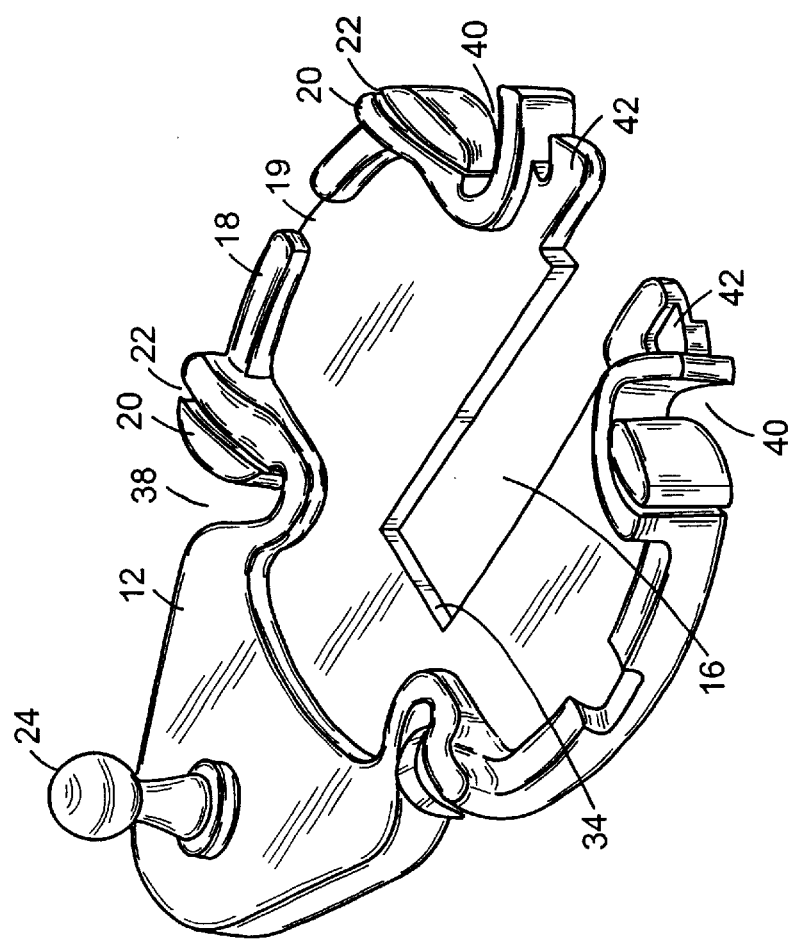
FIG. 3 is a top perspective view of the stabilizer in accordance with the preferred embodiment of the invention having the end portion removed.
Figure 5:
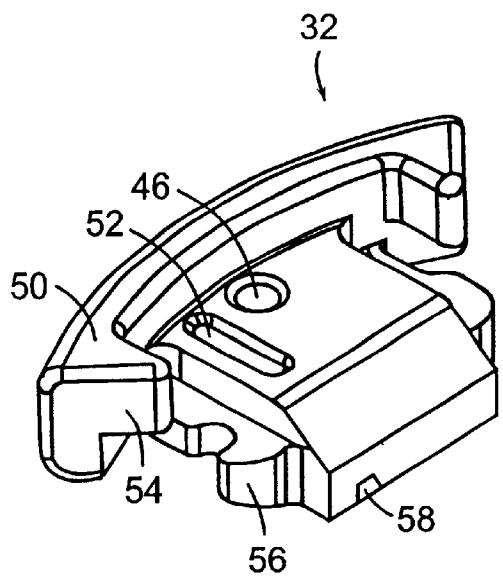
FIG. 5 is a top perspective view of the end portion of the stabilizer in accordance with the preferred embodiment of the invention.
Figure 6:
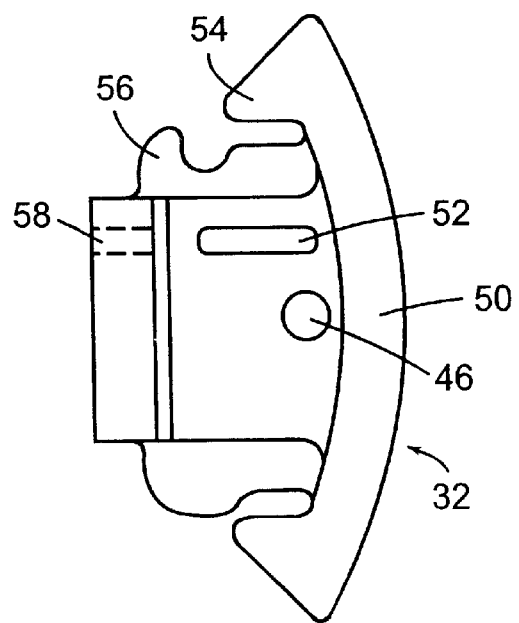
FIG. 6 is an enlarged top view of the end portion of the stabilizer in accordance with the preferred embodiment of the invention.
Figure 7:
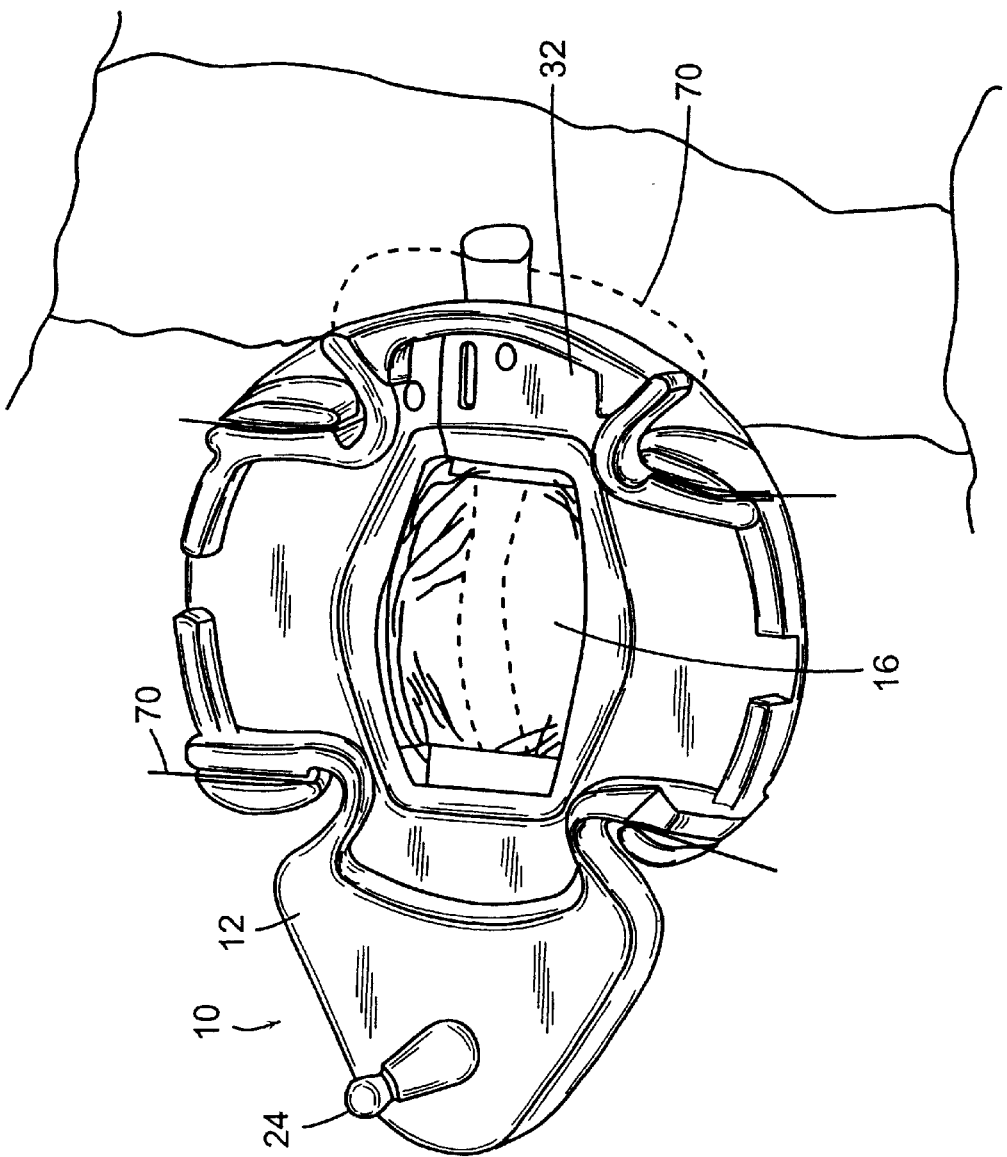
FIG. 7 is an end perspective view of the stabilizer in accordance with the preferred embodiment of the invention showing the tab members in the aperture area and schematically illustrating the compression of a blood vessel.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A preferred embodiment of the invention is illustrated in connection with FIG. 1. A stabilizer 10 includes a platform or base 12 having an aperture area 16 that is closed by a removable end portion 32. The aperture area 16 is positioned in use to expose tissue at a surgical site. The stabilizer 10 can be made with nearly any material, including a metal or a molded plastic material. The stabilizer 10 can be sterilized after each use, or alternatively, can be disposable after one procedure. A handle 30 or articulating arm can be permanently attached to a connector 24 on the base 12 of the stabilizer 10, or as described below in connection with other preferred embodiments, can be detachable.

In a preferred embodiment of the invention, the platform has a substantially ovoid or elongate shape with each side having a width in the range between about 0.75 cm. and 2 cm. and a length in the range of about 3.0 cm and 6 cm. Thus the surface area of the platform is between about 2.25 $cm^2$ and 12 $cm^2$, preferably between about 5 $cm^2$ and 10 $cm^2$. This size fits readily in the incision in the chest of the patient either during typical open chest surgery or less or minimally invasive surgery and can be positioned along nearly any surface of the heart. The upper surface of the base 12 of the stabilizer 10 preferably includes a raised lip area 18 substantially surrounding the sides of the stabilizer 10 and a plurality of spaced apart and raised upstanding holder members 20 having slots 22 associated therewith. As shown, a plurality of drainage areas 19 may be located along the lengthwise dimension of the base to allow fluids to drain from the base 12 during the procedure. A connector 24, such as a ball member, is positioned along the proximal side of the base 12 of the stabilizer 10 and is spaced apart from the aperture area 16. In the preferred form of this invention, the connector 24 is positioned adjacent to the lip area 18 and is releasably attachable to a handle member 30. The remaining distal side of the stabilizer 10 includes a releasable end portion 32 to enclose the aperture area 16.

Additionally, the base 12 preferably includes a plurality of pairs of spaced apart recessed areas 38 and 40 on the sides thereof. The pairs of recessed areas 38 and 40 preferably extend inwardly from the periphery of the base 12 and are aligned generally with the tab members 34 and 36 the ends of the aperture area 16. As shown, the pairs of the recessed areas 38 and 40 preferably decrease in width and curve a small amount inwardly from the periphery of the stabilizer to allow the tapes 70 to be threaded therein. The tapes 70 may be made of nearly any material such as suture, thread or SILASTIC, stretchable material. The recessed areas 38 and 40 assist in retaining the tapes in the desired position prior to threading the tapes into the holding mechanisms 20. In this embodiment, the user may pull the tapes toward the respective ends of the stabilizer to diagonally thread the tapes into the recessed areas 38 and 40. The width of the pairs of recessed areas 38 and 40 are sized to removably and readily receive the connecting tapes 70 therein. The inner surface of the recessed areas are also preferably aligned with the holder members 20 and slots 22 located along the exterior surface of the stabilizer 10 and the distal and proximal ends of the aperture area 16.

The size of the aperture area 16 can be in the range of about 0.1 and 2 cm. in width and about 0.5 and 5 mm in length. The aperture area 16 can be of various configurations including, wider in the center and narrower at the ends adjacent to the connector 24 and the end portion 32 as shown in the preferred form of the present invention. In the preferred form of the present invention, the sides of the aperture area 16 are slightly curved to provide a wider area at the center of the aperture area than at the ends of the aperture area to assist in framing the surgical site for the surgeon as the tissue is exposed. As shown, the aperture area 16 of the stabilizer is formed to include a proximal side and lateral sides that are formed as part of the base 12 and the distal side that is formed by the removable end portion 32. As referenced above, the combined use of the tapes 70 and the tab members 34 and 36 cause the tissue to extend upwardly a small amount into the aperture area.

The distal end portion of the base includes a contact area 42 extending along each side of the aperture area 16. The contact area 42 includes a pair of generally flat, inwardly extending surfaces thereon for the frictional receipt of the end portion 32 thereon. Additionally, a suture hole 44 is located along one side of the contact area to receive a suture 48 that is threaded through a similar suture hole 46 located on the end portion 32. The suture holes 44 and 46 allow the end portion 32 to be fixedly attached to the base 12 via a suture 48 that is threaded through the suture holes 44 and 46. The use of the suture 48 and suture holes reduce the likelihood that the end portion 32 may become disengaged from the base prematurely during the surgical procedure. Once the anastomosis is completed, the surgeon may cut the suture 48 using a blade or other instrument.

The end portion 32 of the stabilizer 10 is sized to be frictionally received on the distal end of the base 12 and to close the distal end of the aperture area 16. The end portion 32 forms the distal end of the aperture area 16 and includes a top raised lip area 50 along the outer periphery thereof that fits adjacent to the raised lip area 18 of the base 12 and the pair of recessed areas 40. The suture hole 46 and a cutting slot 52 are positioned on the top surface of the end portion 32. The cutting slot 52 is located between the suture hole 44 and suture hole 46 to provide the surgeon with an elongate recess to cut the suture 48 in. The sides of the end portion 32 also include upper and lower extensions, 54 and 56 that are sized and positioned to frictionally receive the contact area 42 from the base 12 therein so that the end portion is frictionally retained on the base even after the suture 48 is cut by the surgeon. Although the end portion is preferably frictionally retained on the base 12, it is anticipated that various other mechanisms may be used, such as clips, adhesives or other temporary retaining members. As shown, the upper extensions 54 from the end portion 32 preferably extend inwardly from the raised lip area 50 while the lower extensions 56 extend inwardly and function to guide and retain the contact areas 42 of the base 12 in the desired position. The end portion 32 may also preferably includes a radio-opaque marker 58 thereon or may include radio-opaque materials therein to enable the surgeon to located the end portion 32 of the stabilizer in the event that the end portion is accidentally separated from the base 12 during the procedure.

The bottom surface 14 of the stabilizer 10 includes a pair of tab members 34 and 36 extending downwardly therefrom. The tab members 34 and 36 are preferably shaped as elongate tapered members that taper downwardly and extend from the bottom surface 14 of the stabilizer 10 along the proximal and distal ends of the aperture area 16. The tab members 34 and 36 are also preferably longer than they are wide and are aligned generally perpendicular to the lengthwise dimension of the aperture area 16 and the intended alignment of the blood vessel. In use, tab member 34 is positioned to reduce blood flow from the blood vessel into the surgical site formed by the aperture area 16. The tab member 36 is positioned on the bottom surface of the end portion 32 and is oriented to be positioned downstream of the surgical site formed by the aperture area 16 to prevent the back flow of blood from the blood vessel. In the preferred form of the present invention, the tab member 36 is formed to extend at least partially from the bottom surface of the end portion 32. A plurality of spaced apart gripping surfaces 60 are also located on the bottom surface 14 of the base to assist in maintaining contact between the tissue of the patient and the stabilizer 10.

Alternately, the bottom surface 14 of the base 12 that is in contact with the myocardium may be roughened or abraded to frictionally engage the heart wall around the artery and thereby locally restrict heart motion around the surgical site.

In the preferred embodiment of the present invention, the stabilizer 10 can have a connector 24, such as a ball member from a ball and socket connection, or a similar handle attachment mechanism so that the user can attach a handle 30 to the stabilizer 10 to provide convenient access to the aperture area 16 and facilitate immobilization of the tissue surrounding the artery. The connector 24 can be located along the proximal end portion of the base and is positioned between or adjacent to the tapes relative to the aperture area and also preferably extends above the top surface of the stabilizer 10. This structure exerts little downward force or upward force on the heart on the artery while immobilizing the tissue at the surgical site. Also the anterior-posterior compression of the artery avoids trauma to the artery due to circumferential compression. As shown, the tapes 70 under the bottom surface of the tabs 32 and 36 lifts the artery to form an occlusion by compressing the artery between the tissue captured by the tape and the bottom surface of the stabilizer 10.

A preferred embodiment of the invention can be used at a surgical site to perform an anastomosis during a bypass procedure. In this particular procedure for a coronary graft without cardiopulmonary bypass, a proximal portion of the LIMA is dissected from the chest wall to expose an end to be grafted onto a grafting site on the coronary artery. Alternately, the saphenous vein may be harvested from a leg of the patient for use as the bypass conduit. The exposed surface of heart is undergoing substantial three-dimensional movement during the procedure as the heart is allowed to continue beating in the usual manner. Blood flow in the vessel can be occluded with a clamp. In this example, a connector such as a suture, thread, cord or silastic tape 70 is threaded through myocardium surface under the coronary artery on opposite sides of the desired grafting site. The stabilizer 10 preferably serves to immobilize the grafting site using the platform portion of the stabilizer and the connecting tape 70 which is stretched and attached to a holder member 20 including one or more slots 22 in the peripheral edge of base 12. As described in greater detail below, the ends of the tapes 70 can be manually positioned in the slots 22 to allow the user to adjust the tension in the tapes or threads. The stabilizer 10 is also preferably secured at the site by attaching the stabilizer to the handle 30 or arm and to a chest retractor or other implement. Therefore, the grafting site preferably undergoes a minimal amount of movement relative to the stabilizer in any direction during the surgical procedure.

Figure 9:
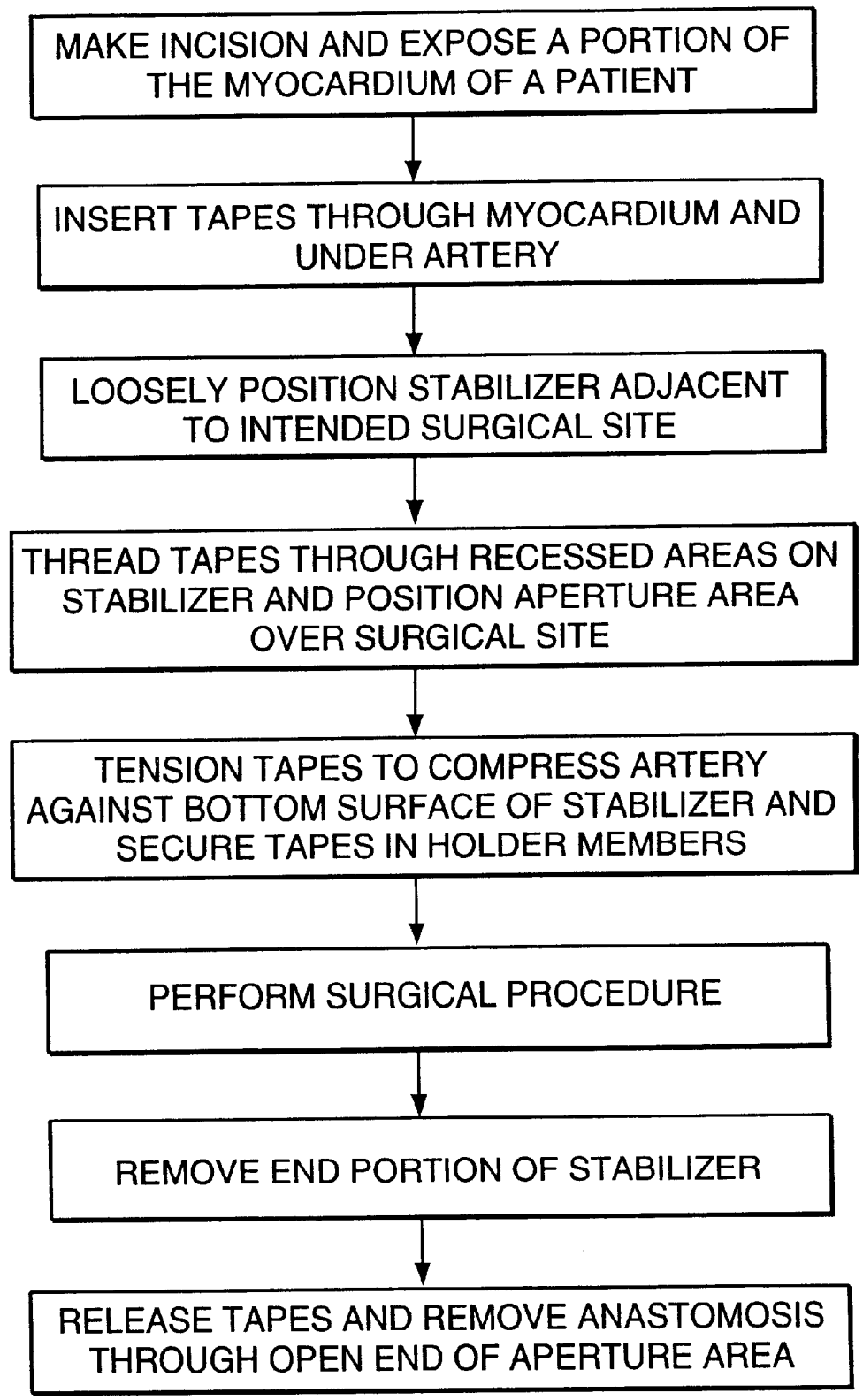
FIG. 9 is a schematic diagram illustrating a surgical procedure in accordance with the preferred form of the present invention.

In the preferred procedure as diagrammatically illustrated in FIG. 9, the tapes 70 are inserted in the myocardium with a blunt needle approximately 1–2 cm apart. The tapes are inserted into the myocardium beneath the desired coronary artery a sufficient distance to include a portion of the tissue adjacent to the artery so that the artery is not excessively constricted during the following procedure. The stabilizer 10 is initially positioned loosely adjacent to the desired surgical site. Once the tapes 70 are pulled through the tissue, the tapes are threaded into the respective recessed areas 38 and 40 on the exterior of the stabilizer 10. The stabilizer is then moved into the desired position and the tapes 70 are tensioned through the recessed areas 38 and 40 to draw tissue against the tab members 34 and 36 up into the aperture area 16. The tensioned tapes are then connected to the slots 22 of the on the holding members 20 of the stabilizer 10 to compress the artery and occlude blood flow distally or upstream of the grafting site and proximally or down stream of the grafting site. The stabilizer 10 is then locked into the desired positioned adjacent to the desired surgical site to assist in the retention of the desired tissue in the aperture area 16 by locking the stabilizer 10 relative to the handle 30 and relative to the chest retractor. The tension in the tapes can be adjusted during the procedure to minimize blood loss at the site and to temporarily verify the flow of blood through the grafted blood vessel.

After the procedure is complete, the stabilizer 10 may be easily removed from the surgical site. In the preferred embodiment, the suture 48 may be cut and the end portion 32 may be removed from the base 12. The tapes 70 may then be released from the slots 22. Once the end portion 32 is removed and the tapes are released, the base 12 includes an open ended aperture area 16 to enable the completed anastomosis to be removed therefrom. This is accomplished by releasing the stabilizer from the locked position relative to the handle 30 and/or the chest retractor and moving the base 12 of the stabilizer relative to the anastomosis. Thereafter, the stabilizer may be reused on another location of the heart by the surgeon. The stabilizer 10 may be reused on the same patient by retying a portion of suture through the suture holes 44 and 46. The stabilizer 10 may then be moved to the next desired location on the heart of the patient and the steps set forth above may be repeated.

Although the use of the stabilizer has been described in connection with a particular bypass procedure, it can also be used in other procedures such as bypass operations involving the diagonal, right or other coronary artery or in surgery for other organs or tissues where movement at the site can interfere with the procedure.

Alternative embodiments involve opening of the chest and positioning the stabilizer at any exposed site on the heart wall or surrounding areas to immobilize the operative site. The stabilizer serves to isolate the site and limits motion at the surgical site due to respiratory movement of the lungs or the pumping motion of the heart.

Figure 8:
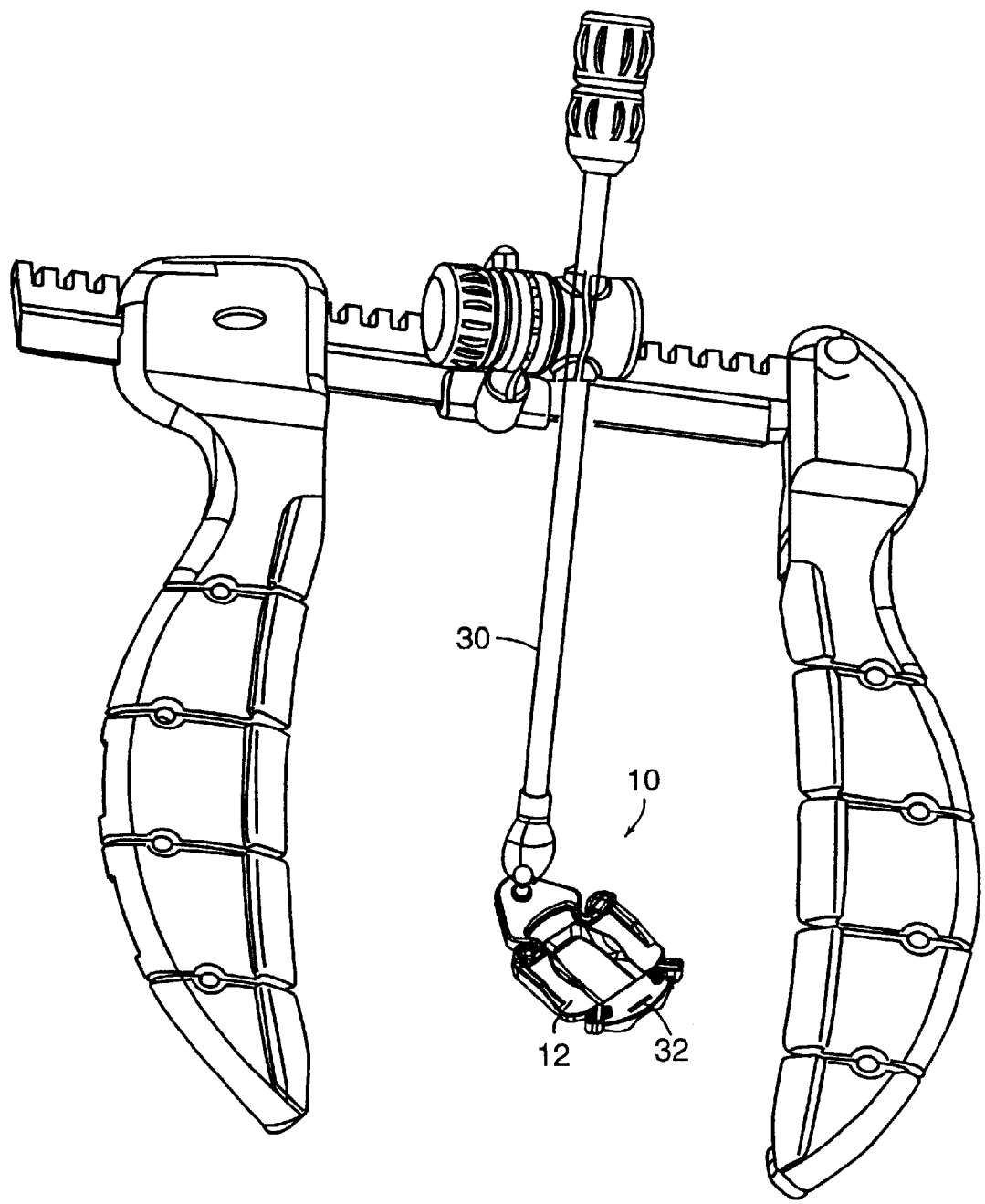
FIG. 8 is a perspective view of a chest retractor and handle supporting a stabilizer in accordance with the invention.

In the preferred embodiment, a retractor system or frame manufactured by Genzyme Surgical Products is illustrated in FIG. 8 to support a stabilizer in accordance with the invention.

While this invention has been particularly shown and described with references to preferred embodiments thereof, it will be understood by those skilled in the art that various changes in form and details may be made therein without departing from the spirit and scope of the invention as set forth in the appended claims.

What is claimed is:

1. A surgical device for a coronary bypass procedure comprising:

a generally rigid stabilizer having a platform area having a length dimension a width dimension and including a base portion and an end portion wherein the base portion and end portion form an outer peripheral surface that encloses an aperture area defining an operative site wherein the aperture area includes a proximal end, a pair of sides and a distal end and the base portion includes a pair of inwardly extending slot members that extend inwardly from the outer peripheral surface to a location generally adjacent to the sides of the aperture area and the end portion is removably retained on the base portion adjacent to the distal end portion of the aperture area and extends between the extending slot members of the base portion.

2. The surgical retractor of claim 1, having raised sidewall elements disposed along the longitudinal dimension of the stabilizer.

3. The surgical retractor of claim 2, wherein the raised sidewall elements have at least one slot therein to frictionally grip an end of a flexible connector and are positioned in general alignment with the slot members.

4. The surgical retractor of claim 1, further including a flexible connector wherein the flexible connector is adapted to extend through the tissue of a patient and the slot members and the stabilizer includes a pair of holders and the flexible connector is retained in a pair of holders on the stabilizer and in general alignment with the slot members.

5. The surgical retractor of claim 1, wherein the stabilizer includes at least one tab member adjacent to the aperture area and the tab member extends downwardly from the bottom surface of the stabilizer and is adapted to compressingly contact the tissue of a patient.

6. The surgical retractor of claim 1, wherein the stabilizer has a plurality of pairs of slot members extending inwardly from the outer peripheral surface thereof and the pairs of slot members are adapted to receive the ends of a flexible connector therein and under the stabilizer such that the connector positions tissue at the surgical site within the aperture area.

7. The surgical retractor of claim 1, further including one or more flexible connectors wherein the flexible connectors extend beneath the stabilizer and through the slot members and are adapted to extend through the tissue of a patient to draw the tissue of a patient into the aperture area and wherein the flexible connectors are releasably connected to the stabilizer via a plurality of tab members that are positioned generally adjacent to the ends of the aperture area.

8. The surgical retractor of claim 1, wherein the stabilizer further includes a raised connector thereon and the raised connector is sized to receive a handle member connected thereto.

9. The surgical retractor of claim 1, wherein the end portion of the stabilizer is frictionally received on the base of the stabilizer.

10. The surgical retractor of claim 1 wherein said end portion is retained on the base by a connecting member that is severable to release the end portion from the base of the stabilizer.

11. A surgical device for a coronary bypass procedure comprising:
   a generally rigid stabilizer having a top surface and a bottom surface and platform area having a length dimension and a width dimension and said platform area includes an outer peripheral surface that encloses an aperture area defining an operative site wherein the aperture area includes a proximal end, a pair of sides and a distal end and a pair of inwardly extending slot members extending inwardly from the outer peripheral surface and adjacent to the sides of the aperture area and a pair of downwardly extending rigid tab members extending from the bottom surface of the platform area adjacent to the ends of the aperture area and the tab members are oriented generally perpendicular to the sides of the aperture area.

12. The surgical retractor of claim 11, having raised sidewall elements disposed along the entire outer peripheral surface of the top surface of the stabilizer.

13. The surgical retractor of claim 12, wherein the top surface includes at least one holder element having a slot member associated therewith to frictionally grip an end of a flexible connector.

14. The surgical retractor of claim 11, further including a flexible connector wherein the flexible connector is adapted to extend through the tissue of a patient and the top surface of the stabilizer includes a pair of holder elements and the flexible connector is retained in a pair of holder elements on the stabilizer and is generally aligned with the tab members.

15. The surgical retractor of claim 11, wherein the stabilizer includes a removable end portion adjacent to the distal end of the aperture area and the end portion is releasable to allow tissue positioned in the aperture area to be removed therethrough and the end portion includes a downwardly extending tab member such that at least one of the downwardly extending tab members is removable from the stabilizer.

16. The surgical retractor of claim 11, wherein the stabilizer has a plurality of pairs of slot members extending inwardly from the outer peripheral surface thereof and the pairs of slot members are adapted to receive a flexible connector therein and under the stabilizer such that the connector assists in positioning the tissue at the surgical site within the aperture area.

17. The surgical retractor of claim 11, further including one or more flexible connectors wherein the flexible connectors extend beneath the stabilizer and are adapted to extend through the tissue of a patient and slot members of the stabilizer in general alignment with the tab members to draw the tissue of a patient into the aperture area and wherein the flexible connectors are releasably connected to holder elements on the top surface of the stabilizer.

18. The surgical retractor of claim 11, wherein the stabilizer further includes a raised connector thereon and the raised connector is sized to receive a handle member connected thereto.

19. The surgical retractor of claim 11, wherein the stabilizer includes a base portion and an end portion and the end portion of the stabilizer is frictionally and removably received on the base portion of the stabilizer to enclose the aperture area.

20. The surgical retractor of claim 11 wherein said end portion is retained on the base portion by a connecting member that is severable to release the end portion from the base portion of the stabilizer.

21. A surgical retractor comprising:
   a retaining element having a generally rectangular platform section wherein said platform section has a length dimension and a width dimension and wherein said lengthwise dimension is formed by a pair of laterally extending members and said width dimension and said laterally extending members form an aperture area having a proximal end, a distal end and a pair of sides and wherein said aperture area is generally ovoid shaped to provide a wider area at the center of the aperture area and sized to allow the formation of a graft at a surgical site therein and is enclosed by an outer peripheral surface the extends along the outer periphery of the platform section;
   an end portion that is removably retained on the laterally extending members adjacent to form the distal end portion of the aperture area;
   a plurality of slot members extending inwardly from the outer peripheral surface of the platform section and adjacent to the ends of the aperture area;
   a pair of holder members on said platform section and wherein said holder members are generally aligned with said slot members.

22. The surgical retractor of claim 21 further including a raised connector and said raised connector is sized for attachment to a handle member to allow for the application of a tissue restraining force against the surgical site by said retaining element.

23. The surgical retractor of claim 21 further including a flexible connector removably attached to said holder members wherein said flexible connector is interconnected with said retaining element to allow for the application of a tissue restraining force against the surgical site adjacent to said aperture area.

24. The surgical retractor of claim 21 further including a pair of tab members extending downwardly from a bottom surface of the retaining element wherein the tab members are aligned with the proximal end and distal end of the aperture area.

25. The surgical retractor of claim 21 further including a tab member extending downwardly from a bottom surface of a removable end portion of the retaining element wherein the tab member is aligned with the distal end of the aperture area.

* * * * *